(12) United States Patent
Willette et al.

(10) Patent No.: US 11,918,715 B2
(45) Date of Patent: Mar. 5, 2024

(54) POLARIZED LED FILTRATION SYSTEM

(71) Applicant: Triatomic Environmental, Inc., Jupiter, FL (US)

(72) Inventors: Christopher C. Willette, Jupiter, FL (US); Aaron Engel, Dollard-des-Ormeaux (CA)

(73) Assignee: Triatomic Environmental, Inc., Jupiter, FL (US)

( * ) Notice: Subject to any disclaimer, the term of this patent is extended or adjusted under 35 U.S.C. 154(b) by 388 days.

(21) Appl. No.: 17/164,300

(22) Filed: Feb. 1, 2021

(65) Prior Publication Data
US 2021/0236682 A1 Aug. 5, 2021

Related U.S. Application Data

(60) Provisional application No. 62/968,734, filed on Jan. 31, 2020.

(51) Int. Cl.
*A61L 9/20* (2006.01)
*B01D 46/00* (2022.01)

(52) U.S. Cl.
CPC ............ *A61L 9/20* (2013.01); *B01D 46/0028* (2013.01); *B01D 46/0038* (2013.01); *A61L 2202/11* (2013.01)

(58) Field of Classification Search
CPC ... A61L 9/20; A61L 2202/11; B01D 46/0028; B01D 46/0038
USPC .......................................................... 96/224
See application file for complete search history.

(56) References Cited

U.S. PATENT DOCUMENTS

| | | |
|---|---|---|
| 8,505,959 B2 | 8/2013 | Darling, III |
| 9,035,270 B2 | 5/2015 | Graebel |
| 9,416,949 B2 | 8/2016 | Aycock |
| 9,506,634 B1 | 11/2016 | Ellis |
| 9,587,849 B2 | 3/2017 | Schlesinger |
| 10,161,641 B2 | 12/2018 | Goel |
| 10,206,525 B2 | 2/2019 | Huffar |
| 10,714,385 B2 | 7/2020 | Kovalgin |
| 10,731,885 B2 | 8/2020 | Ajax |
| 10,767,879 B1 | 9/2020 | Burnett |
| 10,804,098 B2 | 10/2020 | Raisanen |
| 10,814,030 B1 | 10/2020 | Burnett |
| 10,837,665 B2 | 11/2020 | Ajax |
| 10,866,003 B2 | 12/2020 | Ajax |
| 10,883,175 B2 | 1/2021 | Wiegers |
| 10,928,084 B2 | 2/2021 | Ajax |
| 11,024,523 B2 | 6/2021 | Oosterlaken |
| 11,081,345 B2 | 8/2021 | Suzuki |
| 11,088,002 B2 | 8/2021 | Pierreux |

(Continued)

FOREIGN PATENT DOCUMENTS

CN 203980472 U * 12/2014

*Primary Examiner* — Robert Clemente
(74) *Attorney, Agent, or Firm* — Dentons US LLP

(57) ABSTRACT

A polarized LED filter. The polarized LED filter comprises one or more components which are designed to attract and conglomerate particulates, allowing sub-micron sized contaminants to be easily captured. The polarizing effect delivers high-efficiency filtration with low static pressure. The combination of LED disinfecting arrays and anti-microbial coatings offer surface disinfection which reduces microbial growth, biological blow-off, airborne odors and VOCs while allowing for safer handling and servicing of the HVAC system and filter.

24 Claims, 5 Drawing Sheets

(56) References Cited

U.S. PATENT DOCUMENTS

| | | |
|---|---|---|
| 11,131,474 B2 | 9/2021 | Schwegler |
| 11,162,698 B2 | 11/2021 | Ajax |
| 11,230,766 B2 | 1/2022 | Pierreux |
| 11,232,963 B2 | 1/2022 | Oosterlaken |
| 11,339,476 B2 | 5/2022 | Tsuji |
| 11,476,109 B2 | 10/2022 | Yoshimoto |
| 11,524,090 B1 | 12/2022 | Wagner |
| 2007/0059225 A1 | 3/2007 | Willette |
| 2007/0202021 A1 | 8/2007 | Willette |
| 2009/0010801 A1* | 1/2009 | Murphy ................. B01D 46/10 |
| | | 422/4 |
| 2009/0242408 A1* | 10/2009 | Hsu .......................... B03C 3/60 |
| | | 204/674 |
| 2011/0027130 A1 | 2/2011 | Willette |
| 2013/0192288 A1 | 8/2013 | Willette |
| 2015/0306271 A1 | 10/2015 | Willette |
| 2017/0130981 A1 | 5/2017 | Willette |

\* cited by examiner

POLARIZED LED FILTRATION SYSTEM

CROSS REFERENCE TO RELATED APPLICATION

In accordance with 37 C.F.R 1.76, a claim of priority is included in an Application Data Sheet filed concurrently herewith. Accordingly, the present invention claims priority under 35 USC 119(e) to the U.S. Provisional Application 62/968,734, filed on Jan. 31, 2020, entitled "POLARIZED LED FILTRATION SYSTEM", the contents of which are herein incorporated by reference.

FIELD OF THE INVENTION

The present invention is related to filtration systems; to specialized filters for use with air filtration from heating, ventilating, and air conditioning (HVAC) units; and more particularly, to polarized LED filtration systems and HVAC systems having polarized LED filters.

BACKGROUND OF THE INVENTION

Levels of contaminants, such as algal, fungal, bacterial, viral, and invisible airborne organic chemical and odor contaminants, such as volatile organic compounds (VOCs), in recircuiting recirculating air systems, such as heating, ventilating, and air conditioning (HVAC) units, can be problematic. If left unchecked, such contaminants can be problematic for the many individuals exposed to such air, and to the air system efficiency.

SUMMARY OF THE INVENTION

The present invention is related to systems and methods relating to filtration systems. The systems and methods utilize specialized filters for use with air filtration from heating, ventilating, and air conditioning (HVAC) units. Preferably, the systems and methods comprise polarized LED filtration, and may include an HVAC system having polarized LED filters. The systems, polarized LED filters, and methods are designed to attract and conglomerate particulates, allowing sub-micron sized contaminants to be easily captured. The polarizing effect delivers high-efficiency filtration with low static pressure, allowing for improved airflow with less restriction. The combination of LED disinfecting arrays and anti-microbial coatings provide air and surface disinfection which reduces microbial growth, biological blow-off, airborne odors and VOCs.

Accordingly, it is an objective of the invention to provide specialized filters.

It is a further objective of the invention to provide specialized filters for use with air filtration from heating, ventilating, and air conditioning (HVAC) units.

It is yet another objective of the invention to provide specialized filters for use with LED technology.

It is a still further objective of the invention to provide specialized filters for use with LED disinfecting technology for air filtration from heating, ventilating, and air conditioning (HVAC) units.

It is a further objective of the invention to provide specialized filters for use with UV LED technology for air filtration from heating, ventilating, and air conditioning (HVAC) units.

It is yet another objective of the invention to provide polarized filters for use with air filtration from heating, ventilating, and air conditioning (HVAC) units.

It is a still further objective of the invention to provide polarized filters for use with LED technology for air filtration from heating, ventilating, and air conditioning (HVAC) units.

It is a still further objective of the invention to provide a polarized HVAC filtration system with LED technology incorporated.

It is a still further objective of the invention to provide polarized filters using a power supply ballast which includes an electronic circuit adapted to receive low voltage power in a range of approximately 15-65 alternating current (VAC), preferably 18 VAC to 32 VAC, and operate the LED Light.

Other objectives and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

DETAILED DESCRIPTION OF THE INVENTION

Figure 1:
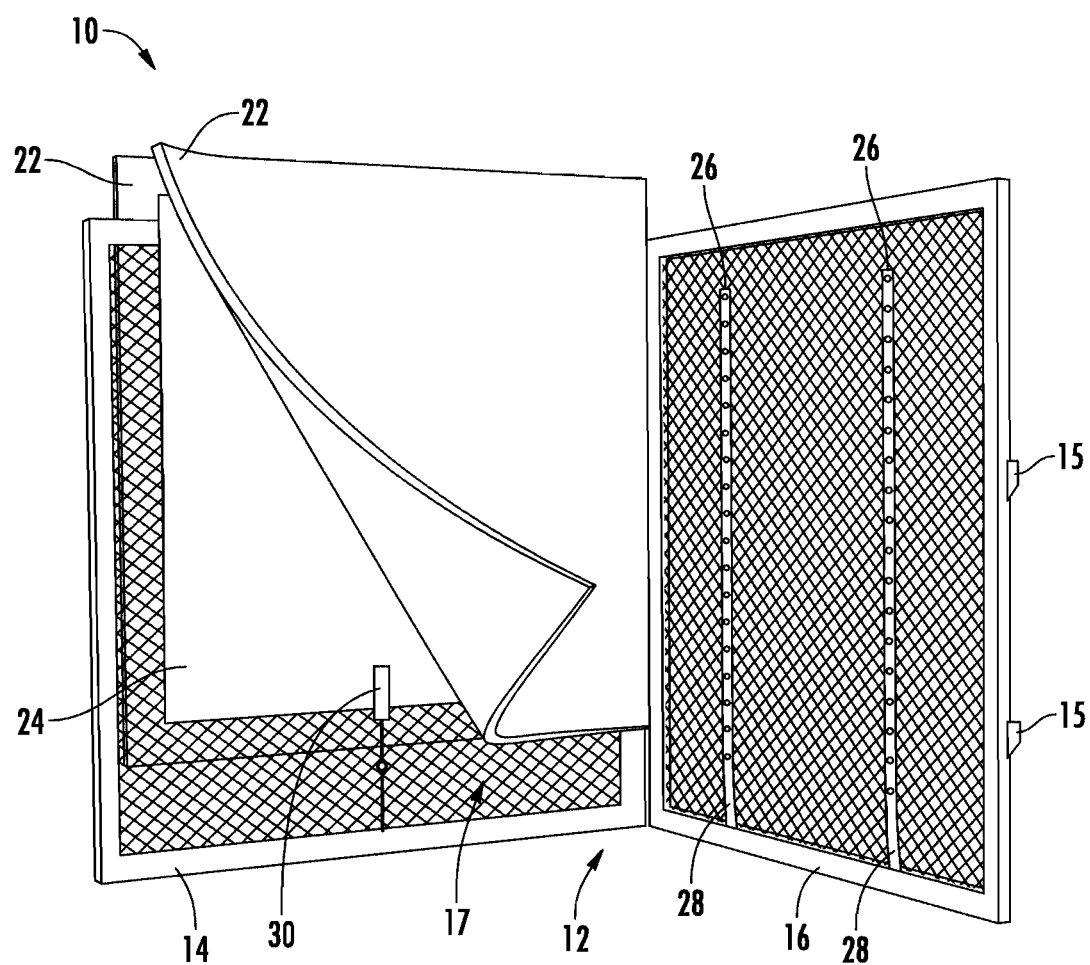
FIG. 1 is an illustrative example of a polarized LED filter.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Figure 2:
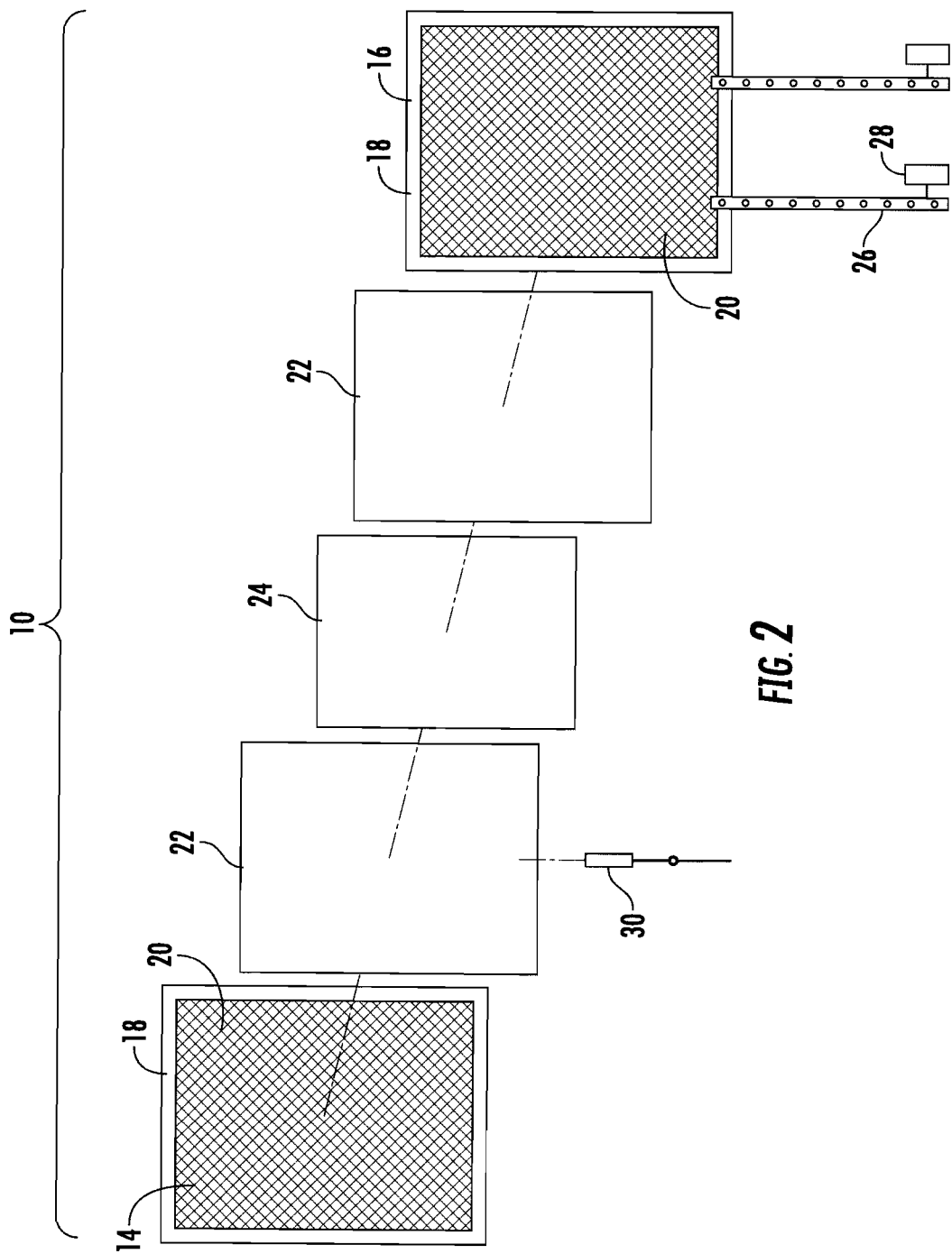
FIG. 2 is an exploded view of the polarized LED filter.

Referring to FIGS. 1 and 2, an illustrative example of a polarized LED filter, referred to generally as polarized LED filter 10, is shown. The polarized LED filter 10 is configured to reduce odors and Volatile Organic Compounds (VOCs), and provide disinfecting LED array for maximum particulate removal and airborne and surface disinfection. The polarized LED filter 10 is further configured to attract and conglomerate particulates, allowing sub-micron sized contaminants to be easily captured. The polarizing effect delivers high-efficiency filtration with low static pressure, allowing for improved airflow with less restriction. The combination of LED disinfecting arrays and anti-microbial coatings provide air and surface disinfection which reduces microbial growth, biological blow-off, airborne odors and VOCs.

The polarized LED filter 10 may comprise a filter 12 configured to house or hold additional components. The filter 12 may comprise a first frame 14 and a second frame 16. Each frame 14 and 16 may include an outer frame border 18 and a screen 20. The outer frame 18 is preferably made of metal, but other materials known to one of skill in the art may be used. The screen may be a diamond cut screen to help maximize airflow performance. The first frame 14 and the second frame 16 may be secured together using fastening members as known to one of skill in the art, and may include screws or nails. Preferably, the filter 12 is configured having a clam-shell orientation. In this orientation, the first frame 14 and the second frame 16 may be secured or linked together via a hinge (not shown), allowing the first frame 14 and the second frame 16 to swing relative to the other. The first frame 14 and the second frame 16 may be secured together using securing members 15, such as a clamp, or snap fitting.

The filter 12 is configured to house or store additional components, each of which is placed in between the first frame 14 and the second frame 16. The first frame 14 and the second frame 16, when secured together may form a housing structure having an interior 17 with sufficient space to store the additional components. The filter 12 may include one or more filter media 22, such as a fiberglass filter media and carbon core 24. The carbon core 24 is preferably an activated carbon. The carbon core 24 may be configured to include or be treated with a light activating catalyst. The catalyst may be blended within or coated onto the carbon core 24. The carbon core 24 may be designed to include multiple, individual cell units. Preferably, the catalyst coating may be a novel two-component composition which forms a new chemical molecule, having photocatalytic action and surface binding and antimicrobial properties. The catalyst composition comprises 1) an organosilane, preferably an organosilane quaternary ammonium, and 2) a photocatalyst, such as titanium dioxide, $TiO_2$. Other photocatalysts may include Zinc Oxide (ZnO), tungsten trioxide ($WO_3$), Zirconium dioxide ($ZrO_2$), or cadmium sulfide (CdS). The composition is believed to be effective by utilizing one or more characteristics. The organosilane imparts positive charge on the composition. The positive charge attracts the negatively charged microbes or contaminants, such as volatile organic compounds (VOCs). The organosilane component is further believed to puncture and chemically kill the microbe and breakdown the contaminants VOCs. Finally, the titanium dioxide (TiO2) is believed to reduce pathogens or contaminant VOCs through the reactive oxidative stress (ROS) process.

The organosilane molecule (Formula 1) has three key elements:

$$X\text{—}R\text{—}Si(OR')3 \qquad \text{(Formula 1)}$$

Wherein: X is a non-hydrolyzable organic moiety. This moiety can be reactive toward another chemical (e.g., amino, epoxy, vinyl, methacrylate, sulfur) or nonreactive (e.g., alkyl; wherein OR' is a hydrolyzable group, like an alkoxy group (e.g., methoxy, ethoxy isopropoxy) or an acetoxy group that can react with various forms of hydroxyl groups present in mineral fillers or polymers and liberates alcohols (methanol, ethanol, propanol) or acid (acetic acid). These groups can provide the linkage with inorganic or organic substrate; and wherein R is a spacer, which can be either an aryl or alkyl chain, typically propyl-[R'=Methyl, Ethyl, Isopropy, R=Aryl or Alkyl $(CH2)_n$ with n 0, 1 or 3].

Illustrative examples of organosilane quaternary compounds in accordance with the present invention include, but are not limited to: 3-(trimethoxysilyl)propyldimethyloctadecyl ammonium chloride; 3-(trimethoxysilyl)propyldidecylmethyl ammonium chloride; 3-(trimethoxysilyl)propyltetradecyidimethyl ammonium chloride; 3-(trimethoxysilyl)propyldimethylsoya ammonium chloride; 3-(trimethoxysilyl)propyldimethyloleyl ammonium chloride; 3-(trimethoxysilyl)propyloctadecyl ammonium chloride; 3-(trimethoxysilyl)propyloleyl ammonium chloride; 3-(trihydroxysilyl)propyldimethyloctadecyl ammonium chloride; and 3-(trimethoxysilyl)propyldocosane ammonium chloride; 3-(trimethoxysilyl)propylmethyldi (decyl) ammonium chloride; 3-chhlorpropyltrimethoxysilane; octadecyltrimethoxysilane; perfluorooctyltriethoxysilane; benzalkonium chloride; glycine betaine; or siltrane compounds (alkanoalmine in combination with organosilicon quaternary ammonium).

The photocatalyst composition may be formed with titanium dioxide ($TiO_2$) in a nano particle form. Accordingly, reference to $TiO_2$ includes titanium dioxide nanoparticles, including $TiO_2$, anatase grade. $TiO_2$ can be doped, or incorporated with other elements, or dopants, to make it more responsive to a wider range of light. In particular, by doping the photocatalyst, the light spectrums in the visible ranges above 400 nanometers can become effective, whereas undoped photocatalysts are only affective up to 365 nm. The elements include, but are not limited to zinc oxide, zirconium dioxide, nitrogen, silicone, silver (Ag), carbon, iron, or copper. As an illustrative example, nitrogen doped titanium dioxide/quaternary ammonium composition allows the catalyst functionality to work in spectrums above 365 nm, such as at 405 nm. By working in spectrums above 400 nm, this allows the photocatalyst to work with visible light sources, such as fluorescent lights, sunlight or LEDS. Use of LEDS in the UV spectrum are more expensive than visible range LEDS. Systems that can function in different light ranges are more cost effective and are more functional over a wider range of light sources beyond the UV based ones. Additionally, $TiO_2$ can be modified with a visible light component such as porphyrins, including but not limited to meso-tetrakis(4-sulfonatopheny)porphyrin or Fe(III) meso-tetra (4-carboxyphenyl)porphine chloride. This porphyrin modified TiO2 nano particle (porphyrin-$TiO_2$) can then be treated to adsorptive surfaces such as activate carbon and also used in combination with the organosilane surface binding molecule.

As such, the catalyst composition may function both as an organosilane surface binding molecule and a photocatalytic molecule. The composition may therefore form a multifunctional, anti-microbial biocide/contaminant VOCs degrader having several of the following characteristics: 1) a silane base which serves to combine the molecules together and to other surfaces, such as to the surface of the activated carbon; 2) the molecule contains a positively charged component for attracting microbes or contaminant VOCs towards the molecule; 3) a long chain for mechanically and chemically puncturing, as well as chemically neutralizing microbes and degrades/breaks down contaminant VOCs; and 4) a photocatalytically activating molecule, creating a reactive oxygen and hydroxyl radical environment which oxidizes microbes, degrades contaminant VOCs, and catalyzes chemical compounds via the light activated catalytic process.

As an illustrative example, the catalyst may comprise 1 part organosilane to 2 parts light activated photocatalyst, and water, QS w/concentrated composition to desired effective concentration. The 1 part organosilane may be quaternary ammonium. In an illustrative example, the photocatalyst composition may be composed of 2 parts $TiO_2$ to 1 part organosilane quaternary compound to form a concentrated compound. The concentrated compound may then be diluted approximately 20:1 for an applied concentration dosage of approximately 1000-1250 ppm.

The polarized LED filter 10 further includes an electromagnetic radiant energy generating source, preferably an ultraviolet light emitted by an ultraviolet light source, illustrated herein as a UV LED light array 26 with LED driver 28. The electromagnetic radiant energy generating source, illustrated as UV LED light array 26, may be designed to include electromagnetic irradiation over a spectrum. For example, polarized LED filter 10 may include a UV LED light array 26 designed to provide a UV spectrum (100 nm-700 nm) using various light sources, such as UV-C lamps, UV Spectrum, discrete spectrum LED or pulsed UV lamps. The light source may be configured to be dynamic, i.e. a dimmable UV lamp or LED may be used as an energy saving means. A light source producing light waves in the range of above 250 nm to 480 nm may be used, such as 275 nm, 365 nm, or 405 nm.

Figure 4A:
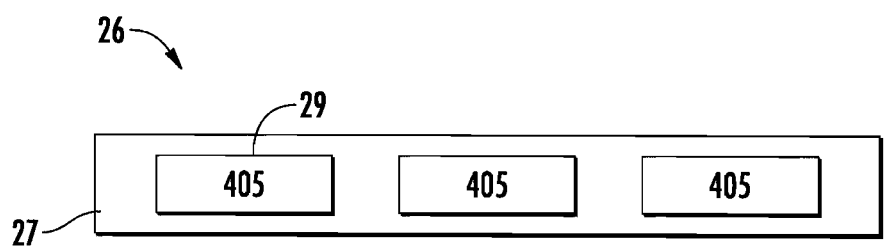
FIG. 4A is an illustrative example of a UV LED strip.
Figure 4B:
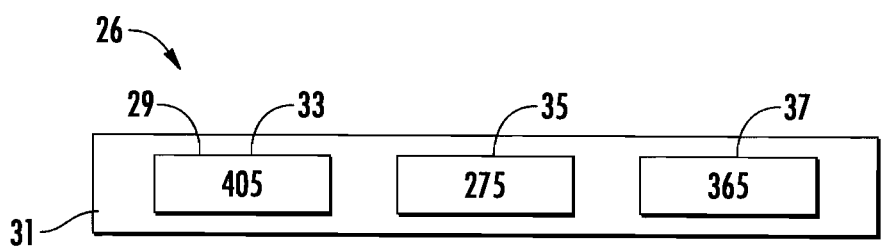
FIG. 4B is an illustrative example of a hybrid UV LED strip.

Alternatively, the UV LED light array 26 may be a UV LED strip comprising a flexible circuit board 27 with surface mounted UV LED diodes 29 (optionally, with adhesive for securing to a surface) to produce UV light, see FIG. 4A. As shown in FIG. 4A, the UV LEDs all emit a single frequency, such as 405 nm. FIG. 4B illustrates a hybrid UV LED strip 31 comprised of UV LED diodes 29 emitting different frequencies, such as a frequency of 405 nm (diode 33), a frequency of 275 nm (diode 35), and a frequency of 365 nm (diode 37). Accordingly, the polarized LED filter 10 may be configured to expose one or more surfaces to UV light of different UV wavelengths. The polarized LED filter 10 may be comprised of control units (not shown) to 1) expose one surface area or hardware component or device to a specific UV wavelength (say 405 nm) and another surface area or hardware component or device to a second or third, different UV wavelengths (275 nm or 365 nm), 2) cause the hybrid UV LED strip or array 31 to emit different UV wavelengths at different times or for different amounts of time, or 3) provide cycles of exposure to one or more UV wavelengths. The polarized LED filter 10 may be designed to emit light continuously or in pulses, or intermittingly based on predetermined times.

Typically, the UV LED light array 26 requires 12, 18 or 24 volts DC, using a line voltage power supply (inverter) to convert power from 120 thru 277 volts AC to DC to power the UV LED light array 26. Alternatively, the polarized LED filter 10 may be configured to use the 24 VAC power from the HVAC and to create the 12, 18 or 24 VDC needed to power the LED strip 31, thus eliminating the requirement of having a special power supply (inverter). Accordingly, the polarized LED filter 10 may include a power supply ballast for the UV LED light array 26. The power supply driver includes an electronic circuit adapted to receive low voltage power in a range of approximately 15-65 alternating current (VAC), preferably 18 VAC to 32 VAC, and operate the UV LED light array 26 thereby. The power supply may be comprised of a low voltage electronic circuit designed to operate the UV LED light array 26. The extended range low voltage power supply is intended to receive its power source from the twenty-four (24) VAC low voltage source found within typical residential air and light commercial air handling units (AHU's). This power source is typically the source that powers the thermostat and controls of the air handling unit and is fed from a low voltage transformer that takes the high voltage from the main power supply of the air handling unit and transforms it to a low voltage range for this purpose.

The polarized LED filter 10 further includes a polarization or electrostatic attraction generating device, illustrated herein as an electrode probe 30. The electrode probe 30 may be placed or attached to the carbon core 24 in such a manner so as to provide a charge, such as voltages above 6,000 volts and no greater than 9,000 volts, such as 7,200 volts. As a result of the static charge, the fibers from the filters 22 and the airborne particles near the fibers take on an electrical charge and become polarized.

Figure 3:
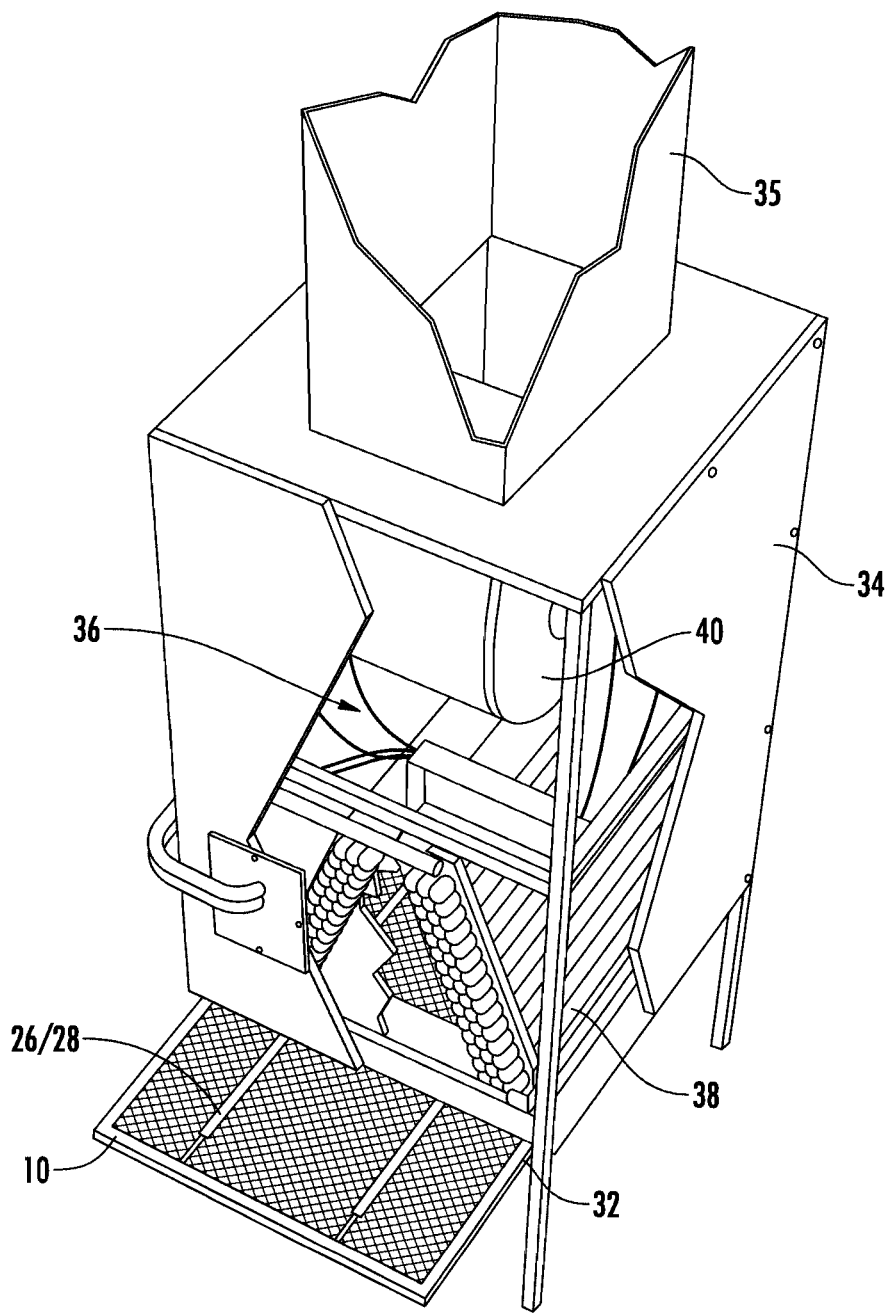
FIG. 3 is an illustrative example of a polarized LED filtration system.

Referring to FIG. 3, the polarized LED filter 10 is shown inserted into a filter rack 32 of an HVAC air handling unit 34 with plenum 35. The partial cutaway view shows the polarized LED filter 10 exposing the interior portion 36 of the air handling unit 34, including evaporator coils 38 and blower 40, to UV light.

The system, which may include polarized LED filter 10 and air handler for units for HVAC, polarized LED filter 10, and methods may include one or more of the following. The polarized LED filter 10 may be made to any size required. Most common HVAC filter sizes are typically 1". The clam-shell filter 12 slides into the standard HVAC filter rack 32. Use of the polarized LED filter 10 may replace the traditional 1" pre or throw-away filter or 4" media filter. A strong but harmless high-voltage charge (i.e. 7,200 volts) travels via the electrode probe 30 into the center of the carbon core 24 coated with the antimicrobial catalyst (organosaline/titanium dioxide composition). This high voltage charge, created by the electrode probe 30, is designed to cause a positive and negative static polarizing charge very near the outermost fiberglass filter media 22.

The fiberglass filter media 22 does not capture particulate through conventional "impingement" (passive mechanism), but rather through the attraction of larger and sub-micron particulate to the positive and negative poles of the fiberglass filter media 22. For those sub-micron particles that may pass through the fiberglass filter media 22, because each contaminant carries a polarized charge (+ and −), they are then attracted to other particles that have passed through the media, agglomerating into a large particulate, allowing them to be easily captured on the fiberglass filter media 22 on subsequent passes. This process allows for high efficiency filtration without the static pressure of conventional filters. Methods, systems, or devices using the polarized LED filter 10 do not rely on thick and restrictive media for particulate impingement; rather such methods, systems, or devices rely on polarized charge to attract and hold contaminants to the media. The carbon core 24 is treated with a proprietary blend of antimicrobial organosilane and titanium dioxide.

The high voltage that passes through the carbon core filter 24, with the carbon-titanium core, allows for a photocatalytic reaction addressing odors and VOCs (Volatile Organic Compounds) that circulate within the envelope of the home or building, as well as having an additional antimicrobial activity via the organosilane process. The UV LED light array(s) 26 can be configured into discrete UV wavelengths, such as 365 nm or 275 nm to create a germicidal wavelength designed to mitigate mold and other microorganisms from growing and passing through the filter media, as well as activating the carbon filter catalyst. A secondary near visible UV wavelength (405 nm) can also be used to further maintain clean filter media, helping to reduce the dangers of having a contaminated filter media which can cause microbial contamination to be re-introduced into the HVAC system during filter replacement or service or mitigate possible cross-contamination when handling a spent or used filter.

SARS-CoV2 Inactivation

Figure 5:
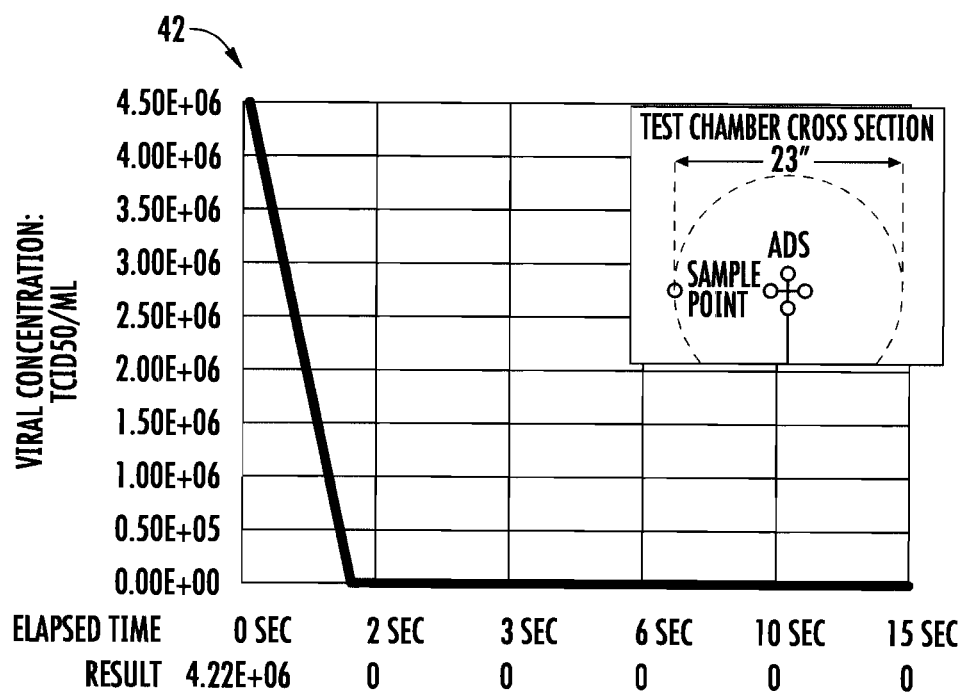
FIG. 5 is a graph illustrating inactivation of SARS-CoV2 in systems using the polarized LED filter.

The carbon catalyst which comprises organosilane and photocatalyst was tested and shown to effectively neutralize >99.99% of SARS-CoV2. In addition, systems using the polarized LED filter 10 showed >99.99% inactivation of the coronavirus in less than two second exposure time, see FIG. 5, graph 42, inactivation of the SARS COVID-19 virus in systems using the polarized LED filter. The test was designed to model exposure time comparative to inactivating the SARS-CoV-2 virus in the moving airstream within an HVAC or ventilation system. The system was tested within a 23" field. Testing was conducted by Innovative Bioanalysis a CAP, CLIA, and AABB certified laboratory (CA, USA).

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A device, comprising:
    a first screen;
    a second screen outermost relative to the first screen;
    a filter extending between the first screen and the second screen;
    a layer extending between the first screen and the second screen, wherein the filter extends between the first screen and the layer;
    a source of an ultraviolet (UV) light configured to direct the UV light toward the filter or the layer; and
    an electrode probe extending between the first screen and the second screen, wherein the electrode probe is coupled to the layer to provide a charge such that the filter or the layer is polarized when the first screen, the second screen, the filter, the layer, the source of the UV light, and the electrode probe extend within a rack of an air handling unit, wherein at least one of:
    (i) further comprising: a first frame hosting the first screen; and a second frame hosting the second screen, wherein the first frame is hingedly connected to the second frame;
    (ii) further comprising: a first frame hosting the first screen; and a second frame hosting the second screen, wherein the first frame or the second frame includes a metal: or
    (iii) the first screen hosts the source of the UV light.

2. The device of claim 1, wherein the source of the UV light is configured to direct the UV light toward the filter.

3. The device of claim 1, wherein the source of the UV light is configured to direct the UV light toward the layer.

4. The device of claim 1, further comprising:
    the first frame hosting the first screen; and
    the second frame hosting the second screen, wherein the first frame is hingedly connected to the second frame.

5. The device of claim 1, further comprising:
    the first frame hosting the first screen; and
    the second frame hosting the second screen, wherein the first frame or the second frame includes the metal.

6. The device of claim 1, wherein the first screen and the second screen enable a clam-shell orientation.

7. The device of claim 1, wherein the first screen hosts the source of the UV light.

8. The device of claim 1, wherein the electrode probe is coupled to the layer to provide the charge such that such that the filter or the layer is polarized and there is 99.99% or more of inactivation of a coronavirus in less than two second exposure time when the coronavirus is present.

9. The device of claim 1, wherein the electrode probe is disposed on the layer.

10. The device of claim 9, wherein the electrode probe is centrally disposed on the layer.

11. The device of claim 1, wherein the electrode probe is coupled to the layer to provide the charge such that the filter is polarized.

12. The device of claim 1, wherein the electrode probe is coupled to the layer to provide the charge such that the layer is polarized.

13. A method, comprising:
    causing a user to extend a first screen, a second screen, a filter, a layer, a source of an ultraviolet (UV) light, and an electrode probe within a rack of an air handling unit, wherein the filter extends between the first screen and the second screen, wherein the layer extends between the first screen and the second screen, wherein the filter extends between the first screen and the layer, wherein the source of the UV light directs the UV light toward the filter or the layer, wherein the electrode probe extends between the first screen and the second screen, wherein the electrode probe is coupled to the layer to provide a charge such that the filter or the layer is polarized, wherein the second screen is outermost relative to the first screen, wherein at least one of:
    (i) wherein the first screen is hosted by a first frame, wherein the second screen is hosted by a second frame, wherein the first frame is hingedly connected to the second frame;
    (ii) wherein the first screen is hosted by a first frame, wherein the second screen is hosted by a second frame, wherein the first frame or the second frame includes a metal; or
    (iii) the first screen hosts the source of the UV light.

14. The method of claim 13, wherein the source of the UV light is configured to direct the UV light toward the filter.

15. The method of claim 13, wherein the source of the UV light is configured to direct the UV light toward the layer.

16. The method of claim 13, wherein the first screen is hosted by the first frame, wherein the second screen is hosted by the second frame, wherein the first frame is hingedly connected to the second frame.

17. The method of claim 13, wherein the first screen is hosted by the first frame, wherein the second screen is hosted by the second frame, wherein the first frame or the second frame includes the metal.

18. The method of claim 13, wherein the first screen and the second screen enable a clam-shell orientation.

19. The method of claim 13, wherein the first screen hosts the source of the UV light.

20. The method of claim 13, wherein the electrode probe is coupled to the layer to provide the charge such that such that the filter or the layer is polarized and there is 99.99% or more of inactivation of a coronavirus in less than two second exposure time when the coronavirus is present.

21. The method of claim 13, wherein the electrode probe is disposed on the layer.

22. The method of claim 21, wherein the electrode probe is centrally disposed on the layer.

23. The method of claim 13, wherein the electrode probe is coupled to the layer to provide the charge such that the filter is polarized.

24. The method of claim 13, wherein the electrode probe is coupled to the layer to provide the charge such that the layer is polarized.

* * * * *